(12) United States Patent
Frenkel et al.

(10) Patent No.: US 6,180,832 B1
(45) Date of Patent: Jan. 30, 2001

(54) PREPARATION OF PEROXYKETALS

(75) Inventors: Peter Frenkel; Ted M. Pettijohn, both of Longview, TX (US)

(73) Assignee: Crompton Corporation, Greenwich, CT (US)

( * ) Notice: Under 35 U.S.C. 154(b), the term of this patent shall be extended for 0 days.

(21) Appl. No.: 09/321,288

(22) Filed: May 27, 1999

(51) Int. Cl.$^7$ ................................................. C07C 409/16
(52) U.S. Cl. ............................................................ 568/561
(58) Field of Search ............................................. 568/561

(56) References Cited

U.S. PATENT DOCUMENTS

| | | | |
|---|---|---|---|
| 3,896,176 | * 7/1975 | Sacrini et al. | 568/561 |
| 3,928,466 | * 12/1975 | Sacrini et al. | 568/561 |
| 3,935,278 | * 1/1976 | Rosenthal et al. . | |
| 3,950,432 | * 4/1976 | Sanchez . | |
| 4,052,464 | 10/1977 | Priddy . | |
| 5,288,919 | 2/1994 | Faraj . | |
| 5,488,176 | 1/1996 | Faraj . | |
| 6,001,767 | * 12/1999 | Frenkel et al. | 502/160 |

* cited by examiner

*Primary Examiner*—Jean F. Vollano
(74) *Attorney, Agent, or Firm*—Shirley S. Ma

(57) ABSTRACT

The process of preparing peroxyketals which comprises reacting a composition comprising ketone with hydroperoxide in the presence of heteropolyacid.

2 Claims, No Drawings

PREPARATION OF PEROXYKETALS

This invention relates to the preparation of peroxyketals by a process comprising reacting a composition comprising an aliphatic ketone with a hydroperoxide in the presence of a heteropolyacid. More particularly, this invention relates to the preparation of water-insoluble peroxyketals by a process comprising (1) reacting an aqueous composition comprising a cycloalkanone with a tertiary alkyl hydroperoxide in the presence of a heteropolyacid and (2) recovering water insoluble peroxyketal by partitioning the aqueous phase containing heteropolyacid from the water-insoluble peroxyketal.

As pointed out in Faraj U.S. Pat. No. 5,288,919 catalysts such as sulfuric acid, sulfonic acid resins and the like have been used to catalyze the reactions of an alcohol such as tertiary butyl alcohol with an organic peroxide such as tertiary butyl hydroperoxide. At column 1, lines 24 to 32, Faraj points out that these catalysts have disadvantages including the corrosion and safety hazards associated with the use of sulfuric acid, catalyst deactivation and deterioration and azeotropic water removal associated with the use of catalyst resins. Faraj indicates that heteropoly acids can advantageously be used in place of the named acids at 20° C. to 150° C., preferably 40° C. to 110° C.

Copending U.S. patent application Ser. No. 08/905,593 discloses that heteropolyacids, in selective amounts, are effective for lowering the onset temperature of decomposition of organic peroxides.

Peroxyketals are generally prepared by the strong acid catalyzed reaction of ketones with hydroperoxides. These reactions have the same type of problems as indicated above by Faraj, i.e. corrosion, safety hazards, deterioration and deactivation, etc. For example, Priddy U.S. Pat. No. 4,052,464 discloses an improved process for the preparation of di-t-butylperoxy ketals which encompass dispersing a ketone, tertiarybutyl hydroperoxide and an acid catalyst in a solvent at a temperature below the decomposition temperature of the desired ketal and under a sufficiently low pressure so as to promote water removal to thereby convert at least a major portion of the ketone to the corresponding di-t-butylperoxy ketal, wherein the improvement comprises employing ethylbenzene as the solvent, conducting the reaction in the presence of an excess tertiarybutyl hydroperoxide, removing water from the reaction by azeotropic distillation with ethylbenzene and removing at least a major portion of the excess tertiarybutyl hydroperoxide by azeotropic distillation.

While it would be desirable to prepare peroxyketals using a heteropolyacid to obtain the advantages alleged by Faraj, it would appear that the teachings of U.S. Ser. No. 08/905,593 and Priddy would dictate against same due to the fact that U.S. patent application Ser. No. 08/905,593 teaches that heteropolyacids reduce the decomposition temperature of peroxyketals such as 1,1-Bis(tertiarybutyl peroxy) cyclohexane from about 92 to 109° C. to 40 to 50° C., and the reaction temperature range that Priddy considers desirable.

The general object of this invention is to provide a technique for using heteropolyacids as catalysts for the reaction of aliphatic ketones, particularly cycloalkanones, with hydroperoxides. Other objects appear herein after.

We have now found that the objects of this invention can be attained for the preparation of peroxyketals, preferably water-insoluble peroxyketals by a process comprising reacting composition comprising ketone(s), preferably cycloalkanone(s) with a hydroperoxide in the presence of a heteropolyacid, preferably followed by recovering water insoluble peroxyketal by separating the aqueous phase (water is a byproduct of this reaction) containing heteropolyacid from peroxyketal. The ketone and hydroperoxide are preferably selected to give rise to a water-insoluble peroxyketal, which can be easily partitioned from heteropolyacid and water. If the system does not contain water, the heteropolyacid attacks the peroxyketal. While the heteropolyacid is in the aqueous phase, it is effective in catalyzing the synthesis of peroxyketals without noticeable decomposition.

Briefly the process of this invention comprises reacting a composition comprising aliphatic ketone(s), preferably cycloalkanone(s), with a hydroperoxide in the presence of a heteropolyacid and recovering peroxyketal by separating the heteropolyacid from peroxyketal.

As indicated above, the instant process is useful for the preparation of peroxyketals, preferably water-insoluble peroxyketals. When tertiary alkyl hydroperoxides of 4 to 10 carbon, such as tertiary butyl hydroperoxide, tertiary amyl hydroperoxide, tertiary octyl hydroperoxide, tertiary decyl hydroperoxide etc., are used virtually any aliphatic ketone can be used, such as acetone, methyl ethyl ketone, cyclohexanone, etc. to produce water-insoluble products. Therefore, tertiary alkyl hydroperoxides are preferred reactants for use in this invention, particularly with cycloalkanones of 4 to 10 carbons.

The mole ratio of aliphatic hydroperoxide to ketone can range from about 1:10 to 10:1, preferably 2:1 to 3:1.

Heteropoly acids generally useful in the present invention are water soluble and have pKa values that are similar in strength to mineral acids.

Of the heteropoly acids useful in the practice of the present invention, those having the formula:

$H_x[X\ M_{12}O_{40}]$ where X is phosphorous or silicon, M is molydenum or tungsten and x is 3 to 4 are preferred. Examples of heteropoly acids in this regard include, without limitation: phosphotungstic acid ($H_3PW_{12}O_{40}$ or PTA); phosphomolybdic acid ($H_3PMo_{12}O_{40}$); silicotungstic acid ($H_4SiW_{12}O_{40}$); and silicomolybdic acid ($H_4SiMo_{12}O_{40}$).

In somewhat greater detail, the process of this invention comprises contacting heteropolyacid, hydroperoxide and alkanone. The heteropolyacid is a non-oxidizing solid reagent which can be easily dissolved in hydroperoxide or cycloalkanones or in any suitable solvent, such as water before combining all the reactants.

The reactants are then mixed at about 0° to 50° C. or slightly higher temperature. After the reaction is complete the aqueous phase containing heteropolyacid is separated from the peroxyketal. If the peroxyketal is water-insoluble, it can be partitioned. If desired the aqueous phase containing unreacted hydroperoxide and heteropolyacid can be recycled for reaction with additional alkanone to form additional amount of the peroxyketal.

The process can be carried out batchwise or continuously.

EXAMPLES

A solution of 0.00027 to 0.00555 moles of the hydrate or phosphotungstic acid (containing 7.31% by weight water) in 0.69 to 0.72 moles of tertiaryalkyl hydroperoxide was added from a pressure equalizing addition funnel over a period of 1 to 2 minutes to a 500 ml round bottomed flask equipped with agitator and thermometer containing 0.3 mol cyclohexanone, at 5–10° C. maintained by dry ice-acetone bath. The temperature of the well mixed reaction mixture was raised by warm water bath to 20° C. to 40° C. and held constant for one hour. The reaction mixture was transferred to a separatory funnel and the phases were allowed to separate (about 30 minutes). The lower aqueous phase was drawn off and the product phase was washed with sodium hydroxide to remove excess hydroperoxide.

Active oxygen content and corresponding purity (concentration) of a peroxyketal were determined by iodometric titration.

The results are set forth in the Tables below wherein TBHP stands for tertiary butyl hydroperoxide, TAHP stands for tertiary amyl hydroperoxide and PTA stands for phosphotungstic acid.

TABLE I

Synthesis of 1,1-bis(t-butylperoxy)cyclohexane

| Example No. | Molar Ratio PTA to cyclohexanone | Molar Ratio of H₂O to PTA | Reaction Temp ° C. | Molar Yield in % |
|---|---|---|---|---|
| 1 | 0.0093 | 161 | 30 | 76.42 |
| 2 | 0.0046 | 320 | 30 | 86.63 |
| 3 | 0.0028 | 524 | 30 | 80.73 |
| 4 | 0.0028 |  | 30 | 81.50 |
| 5 | 0.0046 | 320 | 20 | 84.55 |
| 6 | 0.0046 | 320 | 40 | 86.37 |
| 7 | 0.0046 | 1177 | 30 | 70.20 |
| 8 | 0.0069 | 789 | 30 | 82.10 |
| 9 | 0.0093 | 596 | 30 | 86.38 |
| 10 | 0.0139 | 402 | 30 | 87.86 |
| 11 | 0.0176 | 326 | 30 | 88.75 |
| 12 | 0.0185 | 305 | 30 | 84.93 |

In Examples 1 to 6, 90% tetrabutyl hydroperoxide was used and in Examples 7 to 12, 70% tetrabutyl hydroperoxide. Example 4 was carried out in the aqueous phase recovered from Example 2. The molar ratio of TBHP:cyclohexanone was 2.4 in all examples except Example 4 where the ratio of cyclohexanone:TBHP was 1:2.15.

TABLE II

Synthesis of 1,1-bis(t-amyl peroxy)cyclohexane

| Example No. | Molar Ratio to PTA cyclohexanone | Reaction Temp ° C. | Molar Yield |
|---|---|---|---|
| 13 | 0.0023 | 30 | 72.28 |
| 14 | 0.0046 | 30 | 88.10 |
| 15 | 0.0020 | 30 | 86.56 |

For Examples 13 and 14 molar ratio of TAHP:cyclohexanone was 2.3 and the TAHP concentration was 85%. In Example 15, the aqueous phase from Example 13 was added to the mixture of cyclohexanone and TAHP combined at the molar ratio of 1:2.19.

We claim:
1. A process of preparing peroxyketals which comprises reacting a composition comprising an aliphatic ketone with hydroperoxide in the presence of a heteropolyacid comprising phosphotungstic acid.
2. A process of preparing water-insoluble peroxyketals which comprises reacting an aqueous composition comprising an aliphatic ketone with hydroperoxide in the presence of a heteropolyacid comprising phosphotungstic acid.

* * * * *